(12) United States Patent
Van Der Vliet et al.

(10) Patent No.: US 12,042,309 B2
(45) Date of Patent: Jul. 23, 2024

(54) DEVICE AND METHOD FOR FOLDING AN INSTRUMENT SET IN A PACKAGE

(71) Applicant: R-Solution Medical BV, Barneveld (NL)

(72) Inventors: Mariska Sabine Van Der Vliet, Hilversum (NL); Niels Paul Emerentiana Welling, Oosterbeek (NL)

(73) Assignee: R-Solution Medical BV, Barneveld (NL)

( * ) Notice: Subject to any disclaimer, the term of this patent is extended or adjusted under 35 U.S.C. 154(b) by 0 days.

(21) Appl. No.: 18/235,742

(22) Filed: Aug. 18, 2023

(65) Prior Publication Data

US 2023/0397967 A1 Dec. 14, 2023

Related U.S. Application Data

(63) Continuation of application No. 17/863,536, filed on Jul. 13, 2022, now Pat. No. 11,766,305, which is a
(Continued)

(30) Foreign Application Priority Data

Jul. 7, 2017 (NL) .................................... 2019198

(51) Int. Cl.
*A61B 50/33* (2016.01)
*A61B 50/20* (2016.01)
(Continued)

(52) U.S. Cl.
CPC .............. *A61B 50/33* (2016.02); *A61B 50/20* (2016.02); *A61B 2050/3008* (2016.02);
(Continued)

(58) Field of Classification Search
CPC ......... A61B 50/30; A61B 50/33; A61B 50/20; A61B 2050/3008; B65B 49/00;
(Continued)

(56) References Cited

U.S. PATENT DOCUMENTS

| 6,824,511 B1 | 11/2004 | Bell et al. |
| 2008/0308698 A1 | 12/2008 | Steppe |
| 2011/0005342 A1* | 1/2011 | Treat ...................... G16H 40/40 414/754 |

FOREIGN PATENT DOCUMENTS

| EP | 2411289 A1 | 2/2012 |
| WO | 2010110657 A1 | 9/2010 |

(Continued)

OTHER PUBLICATIONS

International Search Report and Written Opinion—PCT/NL2018/050447 (Jul. 6, 2018).

*Primary Examiner* — Rafael A Ortiz
(74) *Attorney, Agent, or Firm* — The Webb Law Firm

(57) ABSTRACT

Device for folding an instrument tray into a packaging material, comprising a supporting surface for supporting the instrument tray during folding of the instrument tray into the packaging material, a first folding plate and a second folding plate, a movable folding aid for fixing the packaging material over a predefined line portion before and/or during the making of a fold, at least one movable clamp for gripping and moving the packaging material, a control unit for controlling the movement of the first folding plate between its respective first and second positions, the movement of the second folding plate between its respective first and second positions, the movement of the folding aid, and the movement and clamping and release of the at least one clamp.

20 Claims, 6 Drawing Sheets

Figure 1:
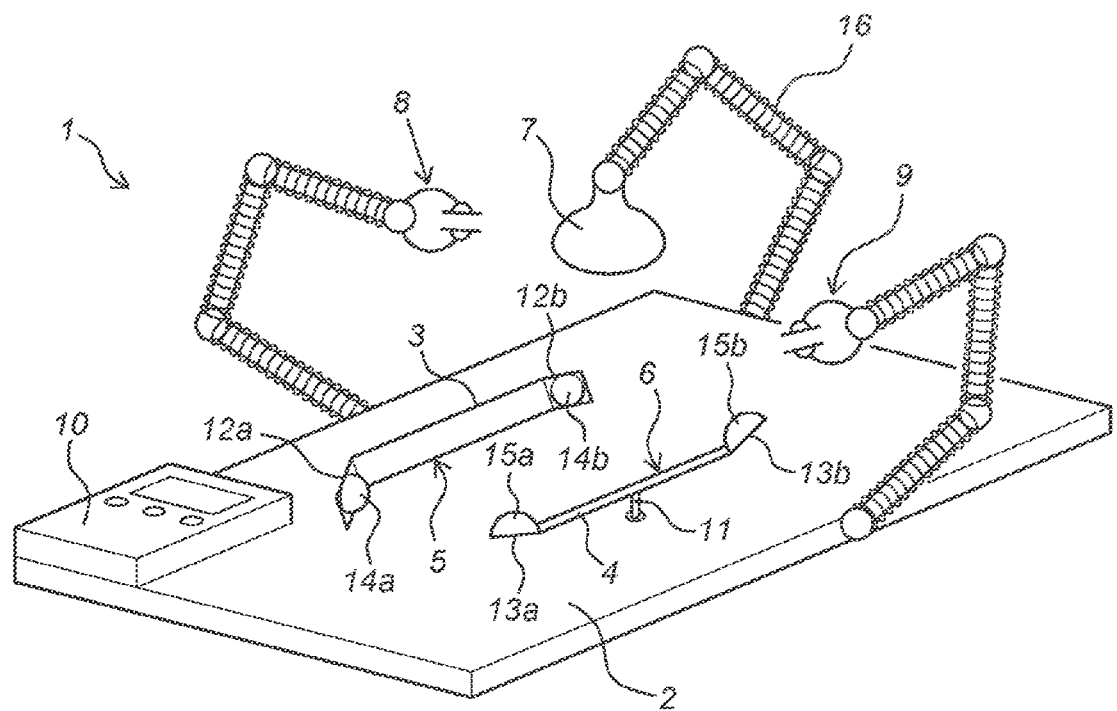

Related U.S. Application Data continuation of application No. 16/628,820, filed as application No. PCT/NL2018/050447 on Jul. 6, 2018, now Pat. No. 11,413,107.

(51) Int. Cl.
 *A61F 13/15* (2006.01)
 *B65B 49/00* (2006.01)
 *A61B 50/30* (2016.01)

(52) U.S. Cl.
 CPC ... *A61F 13/15764* (2013.01); *A61F 13/15772* (2013.01); *A61L 2202/181* (2013.01); *B65B 49/00* (2013.01)

(58) Field of Classification Search
 CPC ............... A61L 2202/181; A61F 13/15; A61F 13/15772; A61F 13/15747
 USPC ................ 206/570, 370; 269/55, 86; 412/17
 See application file for complete search history.

(56) References Cited

FOREIGN PATENT DOCUMENTS

| | | | | |
|---|---|---|---|---|
| WO | WO-2010110657 | A1 * | 9/2010 | ............ B31F 1/0006 |
| WO | WO-2010119884 | A1 * | 10/2010 | ....... A61F 13/15747 |
| WO | WO-2011152346 | A1 * | 12/2011 | ....... A61F 13/15585 |
| WO | 2012085790 | A1 | 6/2012 | |
| WO | WO-2012085790 | A1 * | 6/2012 | ............. A61F 13/15 |

\* cited by examiner

DEVICE AND METHOD FOR FOLDING AN INSTRUMENT SET IN A PACKAGE

CROSS-REFERENCE TO RELATED APPLICATION

This application claims priority to and is a continuation of U.S. patent application Ser. No. 17/863,536 filed on Jul. 13, 2022 and entitled "Device and Method for Folding an Instrument Set in a Package," which claims priority to and is a continuation of U.S. patent application Ser. No. 16/628, 820 filed on Jul. 6, 2018, which issued as U.S. Pat. No. 11,413,107, and entitled "Device and Method for Folding an Instrument Set in a Package," which claims priority to and is a national phase application of PCT/NL2018/050447 filed on Jul. 6, 2018, which claims priority to The Netherlands Patent Application No. 2019198, filed Jul. 7, 2017, the disclosures of which are hereby incorporated herein by reference in their entireties.

The invention concerns a device and a method for folding an instrument tray into a packaging material.

It is important that medical tools and instruments which are used during a medical intervention are supplied in a sterile fashion. For this, the instruments to be used must be successively cleaned, disinfected and sterilised. During mechanical cleaning, a first degree of contamination is removed, whereupon the instruments are disinfected. The cleaned and disinfected medical tools and/or instruments are then inspected and/or assembled, whereupon they may be placed in an instrument tray. This instrument tray is then packed into packaging material. The instrument tray is sterilised after packing. Sterilisation is the essential step whereby the required log reduction in microorganisms takes place in order to be able to present the instrument tray in sterile fashion before and/or during a medical intervention.

For many years, instruments have been packed by specially trained medical personnel at the Central Sterilisation Department (CSA) and/or by an outsourced supplier to a hospital. Packing requires a number of successive actions, wherein it is essential that a predefined folding pattern is performed following a protocol. In order to guarantee the sterility of the instrument in the instrument tray, it is essential that the ends of the packaging material form a structure, wherein the packaging material comprises several turns (tortuous path). The labyrinth-like structure is necessary to prevent microorganisms, particles and similar from being able to penetrate into the instrument tray from the outside via the ends of the packaging material. By making turns in the ends of the packaging material to be folded, a blocking path can be created. Packing the instrument tray following a protocol also means that the operating theatre personnel using the instruments unpack these following a fixed procedure, so that the instruments can be presented in a sterile fashion for use.

Manually folding the instrument trays into the packaging material scarcely offers a reproducible process. It may occur that an instrument tray is not manually positioned in the correct place on the packaging material, whereby during folding it becomes clear that the required overlap of packaging parts cannot be achieved.

There is also a risk that the correct folding pattern is not achieved due to imperfections, wherein for example the minimum number of turns in the labyrinth structure is not achieved, which—as already stated—results in an increased risk of penetration of microorganisms, particles and similar.

If, during unpacking of the instrument tray in the operating theatre, it appears that the packaging material has been incorrectly folded and/or that contamination is present in the instrument tray, the entire instrument set is rejected and cannot be used. If in such a situation there are no identical sterile instrument sets in stock, the operation may be delayed. A further disadvantage of manual packing of instrument sets is that this is physically demanding work, wherein (chronic) wrist, shoulder, elbow, neck and back problems are common complaints.

It is therefore an object of the invention to propose an improved solution for folding an instrument tray into a packaging material.

For this, the invention creates a device for folding an instrument tray into a packaging material, comprising a supporting surface for supporting the instrument tray during folding of the instrument tray into the packaging material; a first folding plate which is movable between a second position in which the first folding plate extends substantially perpendicularly to the supporting surface and thus has a first intersection line with the supporting surface for forming a limit stop against the movement of the instrument tray, and a first position in which the supporting surface is free and flat at the level of the first intersection line; a second folding plate which is movable between a second position in which the second folding plate extends substantially perpendicularly to the supporting surface and thus has a second intersection line with the supporting surface for forming a limit stop against the movement of the instrument tray, and a first position in which the supporting surface is free and flat at the level of the second intersection line, wherein the first intersection line and the second intersection line are substantially parallel to each other; a movable folding aid for fixing the packaging material over a predefined line portion before and/or during the making of a fold; at least one movable clamp for gripping and moving the packaging material; a control unit for controlling the movement of the first folding plate between its respective first and second positions, the movement of the second folding plate between its respective first and second positions, the movement of the folding aid and the movement and clamping and release of the at least one clamp.

The device according to the invention can substantially fully automate the manual packing of instrument trays into packaging material. One advantage of packing instrument trays into packaging material by means of a device according to the invention is that this gives a highly reproducible result. Thus the number of deviating and hence possibly rejected instrument sets in the operating theatre can be reduced.

A further advantage of the device according to the invention is that the chance of soiling and contamination by touching the packaging material is minimised. In particular, touching the inside of the packaging material. i.e. the side facing away from the supporting surface, entails a risk. In manual packing of instrument trays in the packaging material, it regularly occurs that the employee concerned must use his or her hand and/or elbow in order to secure the relatively large packaging material locally, so that the packaging material can be folded in and/or the instrument tray (re)positioned. The device according to the invention ensures that touching the inside of the packaging material, in particular close to the instrument tray, is avoided.

The supporting surface is preferably configured such that it is positioned substantially horizontally during use of the device.

The packaging material may be formed by any suitable packaging material which is substantially permeable to steam, such as for example cloth, linen, crepe paper, SMS material and/or wet laid, non-woven material. Because the first folding plate is at least movable between the first position and the second position, the first folding plate can be utilised optimally during folding of the instrument tray into the packaging material. In the present application, the term "free" means that at this location, there are no parts above the supporting surface which obstruct the placing of a packaging material on the supporting surface. The term "flat" in the present application means that the supporting surface at this location lies in the same plane as it does for its further surface. Preferably, the free part of the supporting surface is at least equal to the surface spanned by the packing material. The aim of the first position is that here, the first folding plate forms no obstacle relative to the supporting surface and/or the packaging material during folding, in particular the first phase(s) thereof. If the first folding plate is positioned in the second position, this forms a limit stop against the movement of the instrument tray. The first folding plate is here not in direct contact with the instrument tray but limits the instrument tray with the interposition of the packaging material. The advantage of this is that the first folding plate makes contact only with the outside of the packaging material, i.e. the side initially facing towards the supporting surface, so there is no risk of contamination.

The function of the second folding plate is initially similar to the function of the first folding plate. In the first position, the second folding plate forms no obstacle relative to the supporting surface. In the second position, the second folding plate is configured to form a limit stop against the movement of the instrument tray. Also, the second folding plate is not in direct contact with the instrument tray, but can fulfil the Delimiting function via the interposition of the packaging material.

It is also conceivable that the first and/or second folding plate, during movement between their respective first and second positions, fulfils an accompanying function of guiding (accompanying) the packaging material during folding.

The first intersection line and the second intersection line are located substantially parallel to each other because the first folding plate and the second folding plate are configured for Delimiting the instrument tray on both sides. Delimiting the instrument tray simplifies the folding of the instrument tray into the packaging material. The folding aid is preferably configured for engaging with the outside of the packaging material, i.e. the side initially facing the supporting surface. The folding aid is configured for preferably temporarily securing the packaging material before and/or during the making of a fold.

The at least one movable clamp is preferably configured for gripping and moving both a single layer of packaging material and a multilayer and/or double- or multi-folded packaging material. The clamp grips the packaging material in the initial unfolded state, preferably only close to the peripheral edges of the packaging material, so that contact between the clamp and the inside of the packaging material is restricted to a minimum.

It is conceivable that the first folding plate in the first position is substantially in line with the supporting surface or is positioned below the supporting surface, and the second folding plate in the first position is substantially in line with the supporting surface or positioned below the supporting surface. The folding plates therefore do not constitute an obstacle during positioning of the packaging material on the supporting surface and prior to folding.

In one possible embodiment, the first folding plate and/or the second folding plate are arranged so as to be translatable relative to the supporting surface. The advantage of this is that it is thus possible to pack different formats of instrument trays into packaging material without the device needing to be structurally adapted for this. With a translatable first and/or second folding plate, a limit stop can be set at the moment that the folding plate grips the instrument tray with the interposition of the packaging material. The movement may for example be achieved by a pneumatic cylinder.

In one embodiment, the device is configured such that the first folding plate and/or the second folding plate is rotatably connected to the supporting surface. The first and/or second folding plate may for example be rotatable about or at the level of the first and second intersection lines respectively.

In another possible embodiment variant, the first folding plate and/or the second folding plate is pivotably connected to the supporting surface. The movement may for example be achieved by a pneumatic cylinder.

In a preferred embodiment of the device, at least the first or the second folding plate is provided with at least one folding part connected to the first or second folding plate around a pivot axis which runs vertically at least in the second position of the first or second folding plate. The use of such a folding part can simplify folding because the folding part can guide the packaging material at the level of the fold to be made. If the device is provided with one or more folding parts, preferably the control unit is configured for controlling the pivoting and/or movement of the folding part.

In one possible embodiment, the device comprises at least one movable magnet provided below the supporting surface for moving the first folding plate and/or the second folding plate between the first position and the second position. Moving the first and/or second folding plate by means of a magnet has the advantage that instrument trays of different dimensions can be folded in relatively simply using the device, without the device needing to be adapted structurally. In this embodiment variant, at least part of the folding plate is formed so as to be magnetic. It is for example possible that the folding plate forms part of a block or another more voluminous body. It is here possible that the magnetic part is contained in the block or body.

Preferably, a pusher element is provided near at least one end of a folding plate for pushing a part of the packaging material extending outside an area limited by the folding plates towards an area located between the intersection lines. Pushing the packaging material in said direction results in an improved fold if the pusher element is used before folding over the side of the packaging material to be folded. The pusher element may here contribute to obtaining an additional turn in the packaging material at the level of the fold, which counters the possibility of penetration of microorganisms from the outside. Preferably, the control unit is configured for controlling the movement of the pusher element.

In one possible embodiment, the pusher element is formed by a protrusion on the folding part. It is also possible that the pusher element forms an integral part of the folding part. In one possible embodiment, the protrusion is situated at a distance from the supporting surface. Experiments have shown that the use of a protrusion, and in particular a protrusion which is situated at a distance from the supporting surface, can further simplify the folding of the packaging material and obtaining of additional turns.

Preferably, the first and the second intersection lines are positioned at a mutual distance which substantially corresponds to a length or width of an instrument tray to be packed, and in particular is between 10 and 80 cm. In particular, this distance is selected such that this corresponds to the instrument trays used in hospitals. The device is preferably configured such that the distance between the first intersection line and the second intersection line is adjustable. Hospitals generally work with a number of different embodiments of instrument trays. The length and/or width of the various embodiments of the instrument trays may vary, whereby it is advantageous to be able to adjust the distance between the first intersection line and the second intersection line, and hence the distance between the first folding plate and the second folding plate. It is conceivable that the distance between the first intersection line and the second intersection line is adaptable by the relative movement of the first folding plate and the second folding plate. It is also conceivable that the distance between the first intersection line and the second intersection line is adjustable by constructing a folding plate in segmented fashion.

The folding aid is preferably shaped such that it has an at least partially flat shape. This is advantageous for temporarily fixing the packaging material over a predefined line portion. Such a folding aid is suitable for temporarily fixing the packaging material before and/or during the making of a fold, because the folding aid does not unnecessarily obstruct the packaging material during the folding process. The folding aid may for example be connected to a movable mechanical arm, wherein the mechanical arm is configured such that, during folding of the instrument tray into the packaging material, the folding aid can be extended and retracted viewed from a top side of the instrument tray. One advantage of this is that the folding aid does not come into unnecessary contact with the inwardly facing parts of the packaging material, and that fewer complex and space-consuming movements are required than in configurations in which the folding aids are moved in a sideways direction.

The folding aid preferably has an at least partially flat shape and further preferably is formed such that, on contact with the packaging material, it does not cause damage to the packaging material. The folding aid therefore has at least partially a rounded or smooth shape.

In a preferred embodiment, the device comprises a supply means for supplying packaging material and a supply means for supplying an instrument tray. In a further preferred embodiment, the supply means for supplying the instrument tray is formed by the at least one clamp. The advantage of the supply means being formed by the at least one clamp is that the device requires no further device components, which is advantageous from a spatial and financial aspect.

In an alternative embodiment however, it is also conceivable that the instrument tray is supplied by means of the folding aid.

In another preferred embodiment, the supply means for supplying packaging material is formed by the at least one clamp. The packaging material may here for example be supplied from a roll, but it is also conceivable that separate packaging materials are supplied. If the packaging material is supplied from a roll, this must be cut off at predefined lengths in order to form a substantially rectangular packaging material. It is also possible that a monitoring means is present, for example in the form of a scanner, to verify that the packaging material is free from contamination.

In a further automated device, it is also conceivable that the packaging material and/or the instrument tray are supplied by means of a transport device such as a conveyor belt.

In a possible embodiment, the device comprises means for establishing a fixing of the packaging material in a predefined position. These may for example be means for supplying adhesive agents such as glues and/or adhesive tape. It is also conceivable that the means are configured for establishing a fixing by means of thermal bonding.

The invention furthermore relates to a method for folding an instrument tray into a packaging material comprising the successive steps: positioning a packaging material on a supporting surface, wherein the packaging material is substantially rectangular and has a respective first, second, third and fourth primary side, wherein the first primary side is located opposite the second primary side and wherein the third primary side is located opposite the fourth primary side:

positioning an instrument tray on the packaging material; gripping and folding the first primary side of the packaging material over the instrument tray to a predefined distance from the second primary side, thus forming a first secondary side; placing a first limit stop which extends from the supporting surface at the level of the first secondary side; gripping and folding the second primary side over the first primary side, thus forming a second secondary side; fixing the packaging material relative to the supporting surface in the vicinity of a side of the instrument tray facing away from the first limit stop; gripping and folding the second secondary side so that the second secondary side is positioned on a top side of the instrument tray and thus forms a tertiary side; placing a second limit stop which extends from the supporting surface at the level of the tertiary side; fixing the packaging material close to the instrument tray over a line portion in line with the third primary side;

folding the third primary side of the packaging material so that the third primary side is positioned at least partially over a top side of the instrument tray;

fixing the packaging material close to the instrument tray over a line portion in line with the fourth primary side; and folding the fourth primary side of the packaging material so that the fourth primary side is positioned on a top side of the instrument tray.

With the method according to the invention, a folded instrument tray is obtained, of which the packaging material has the required labyrinth structure for countering the penetration of microorganisms into the packaging material.

Preferably, the gripping and folding of the second secondary side, so that the second secondary side is positioned on a top side of the instrument tray and hence forms a tertiary side, and the placing of a second limit stop which extends from the supporting surface at the level of the tertiary side, are performed substantially simultaneously. The substantially simultaneous placing of the limit stop has the advantage that the limit stop also fulfils a guiding function during the folding.

Preferably, the method furthermore comprises folding in at least part of the packaging material at the level of the line portion. This step preferably takes place after fixing of the packaging material close to the instrument tray over a line portion in line with the third primary side. This simplifies the successive step of folding the third primary side of the packaging material so that the third primary side is positioned at least partially over a top side of the instrument tray. The folding of at least part of the packaging material at the level of the line portion results in an extra turn of the packaging material at the level of the fold, which counters the penetration of microorganisms. Preferably, the packaging material is folded in on both sides at the level of the line portion.

In a possible variant of the method, this comprises connecting the third primary side and the packaging material on the top side of the instrument tray. This connection may be made for example by means of an adhesive. It is also conceivable that such a connection is created by the use of thermal means.

The method may also comprise connecting the fourth primary side and the packaging material on the top side of the instrument tray. Making the above-mentioned connection brings the advantage that the folded packaging material is fixed in the folded position, so that this can be handled until the connection is actively broken.

The method according to the invention is preferably performed with a device according to the invention. Here, the gripping and folding of the primary and secondary sides of the packaging material is carried out by the at least one clamp, the placing of the first and second limit stop by the movement of the first folding plate and the second folding plate respectively from their first position to the second position, and the fixing of the packaging material is performed by the movable folding aid.

Usually, the positioning of the packaging material on the supporting surface is performed by the at least one clamp. The positioning of the instrument tray on the packaging material is also usually performed by means of the at least one clamp, but may possibly be performed via a conveyor belt.

Figure 3A:
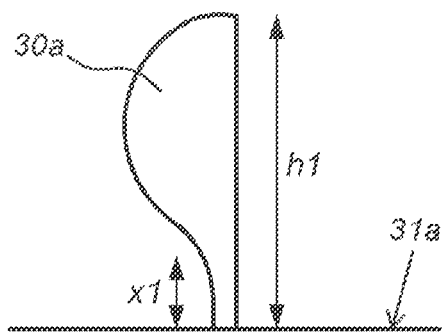
Figure 3B:
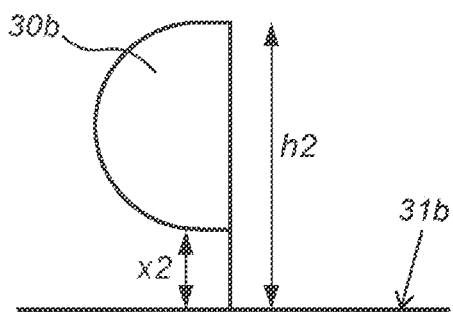
Figure 3C:
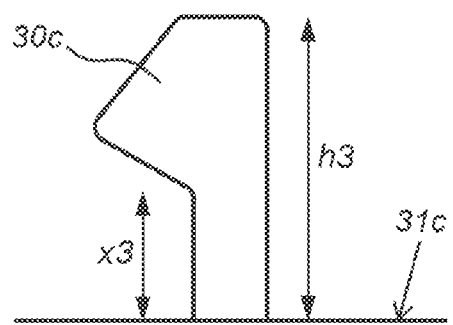
Figure 4A:
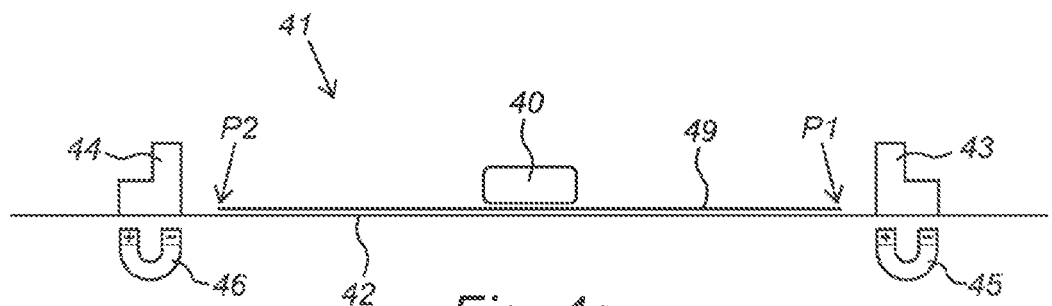
Figure 4B:
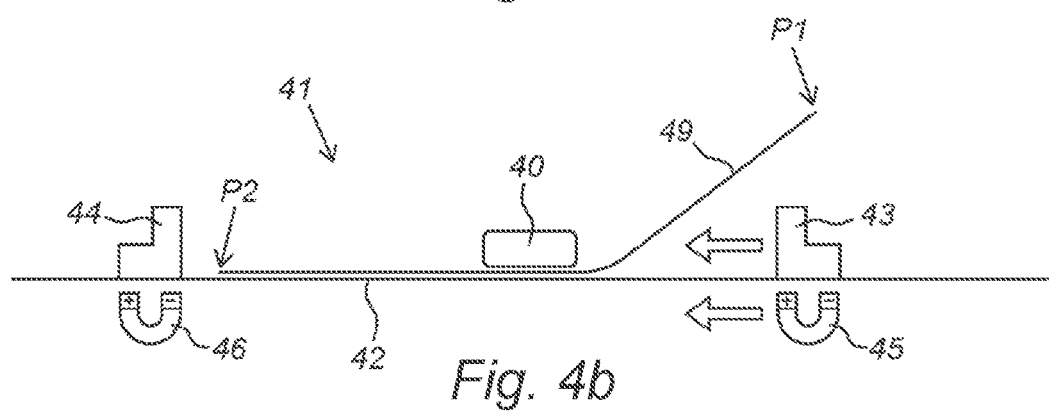
Figure 5A:
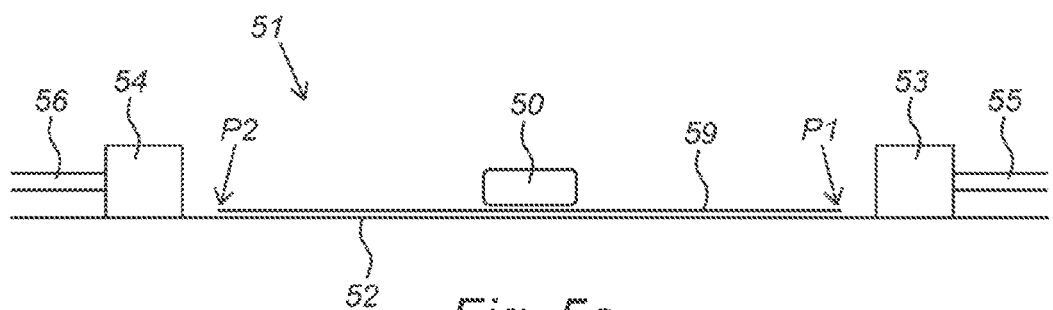
Figure 5B:
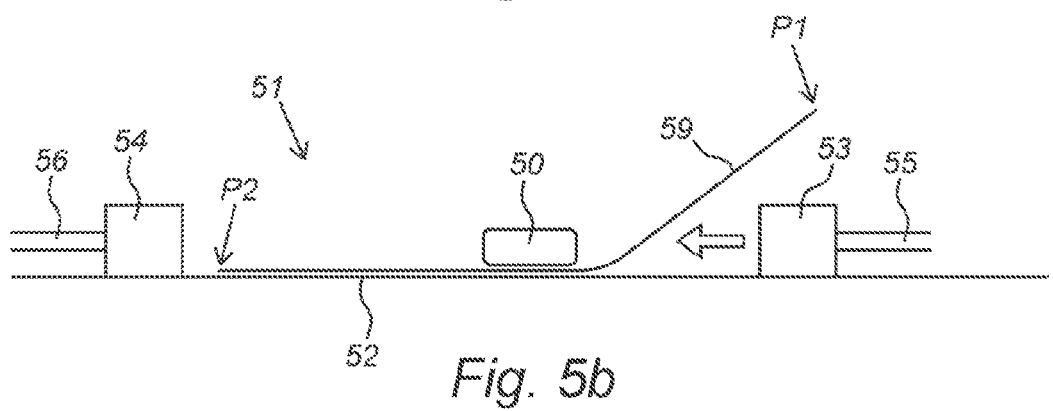
Figure 6A:
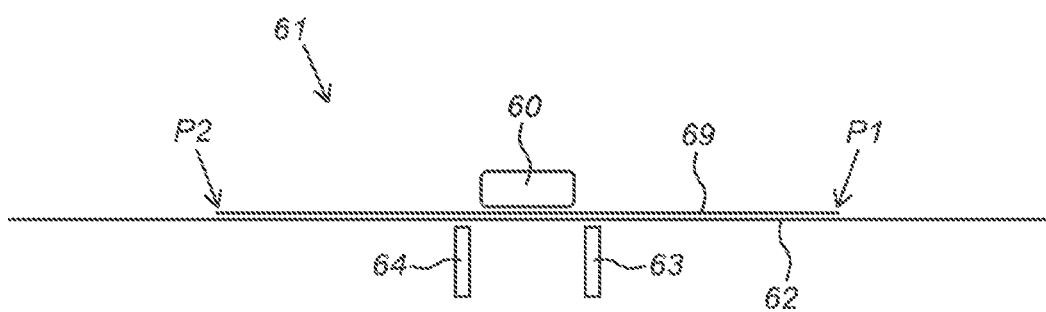
Figure 6B:
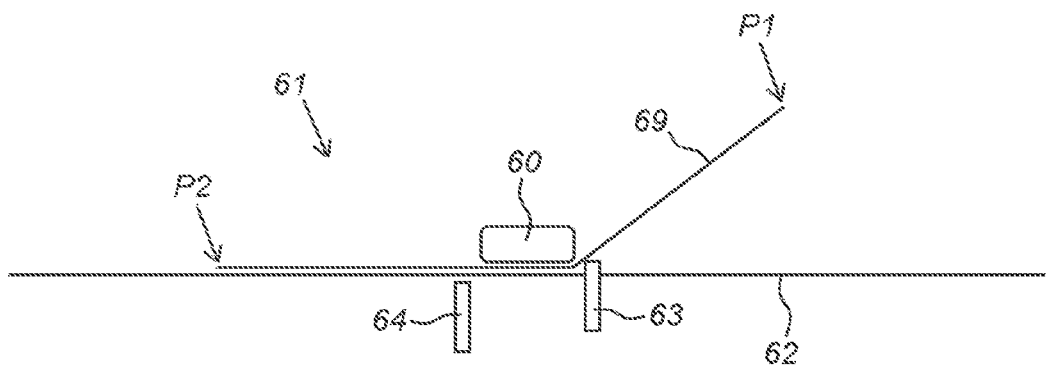

The invention will be explained below with reference to the following figures which depict non-limitative exemplary embodiments. The drawings show:

FIG. 1: a diagrammatic depiction of a possible embodiment variant of a device for folding an instrument tray into a packaging material according to the invention;

FIGS. 2a-i: a diagrammatic depiction of the successive method steps according to the invention carried out by a device according to the invention;

FIGS. 3a-c: a diagrammatic depiction of possible embodiments of a pusher element for use in a device according to the invention;

FIGS. 4a-4b: a diagrammatic depiction of a second possible embodiment variant of the folding device according to the invention;

FIGS. 5a-5b: a diagrammatic depiction of a third possible embodiment variant of the folding device according to the invention; and FIGS. 6a and 6b: a diagrammatic depiction of a fourth possible embodiment variant of the folding device according to the invention.

FIG. 1 shows a device (1) for folding an instrument tray into a packaging material, comprising a supporting surface (2) for supporting the instrument tray (not shown) during the folding of the instrument tray into the packaging material (not shown).

Furthermore, the device (1) comprises a first folding plate (3) which is movable between a first position in which the first folding plate (3) is substantially in line with the supporting surface (2) or positioned below the supporting surface, and a second position in which the first folding plate (3) extends substantially perpendicularly relative to the supporting surface (2) and hence has a first intersection line (5) with the supporting surface (2) for forming a limit stop against the movement of the instrument tray. In the embodiment shown, the first folding plate (3) is situated close to the second position. The device (1) also comprises a second folding plate (4) which is movable between a first position in which the second folding plate (4) is substantially in line with the supporting surface (2) or is positioned below the supporting surface (2), and a second position in which the second folding plate (4) extends substantially perpendicularly relative to the supporting surface (2) and hence forms a second intersection line (6) with the supporting surface (2) for forming a limit stop against the movement of the instrument tray. In FIG. 1, for illustration, the second folding plate (4) is situated in a position between the first position and the second position. The first intersection line (5) and the second intersection line (6) are substantially parallel to each other. The first folding plate (3) and the second folding plate (4) are rotatably connected to the supporting surface (2). The figure shows that the second folding plate (4) can be moved from the first position to the second position by means of a cylinder (11), preferably a pneumatic cylinder (11). The first folding plate (3) is provided with two folding parts (12a, 12b) which are connected to the folding plate (3) around a vertical pivot axis. The second folding plate (4) is also provided with two folding parts (13a, 13b) which are connected around a vertical pivot axis. In the embodiment variant shown, the folding parts (12a, 12b, 13a, 13b) are provided with pusher elements (14a, 14b, 15a, 15b). Each pusher element (14a, 14b, 15a, 15b) is configured for pushing a part of the packaging material extending outside an area limited by the folding plates (3, 4) towards an area located between the intersection lines (5, 6). In the embodiment shown, the pusher elements (14a, 14b, 15a, 15b) are formed by a protrusion on the folding parts (12a, 12b, 13a. 13b), in particular by a protrusion with a curved form.

The device (1) comprises a movable folding aid (7) for fixing the packaging material over a predefined line portion before and/or during the making of the fold. In the embodiment variant shown, the folding aid (7) is connected to a movable mechanical robot arm (16). The folding aid (7) has at least partially a flat shape in order to be able to fix the packaging material over a line portion in an efficient fashion.

In the embodiment shown, the device (1) comprises a first movable clamp (8) for gripping and moving the packaging material, and also a second movable clamp (9) for gripping and moving the packaging material. The first clamp (8) and the second clamp (9) are also configured for supplying the packaging material.

Furthermore, the device (1) comprises a control unit (10) for controlling the movement of the first folding plate (3) between its respective first and second positions, the movement of the second folding plate (4) between its respective first and second positions, the movement of the folding aid (7), and the movement and clamping and release of the first clamp (8) and the second clamp (9).

FIGS. 2a-2i show a diagrammatic depiction of the successive method steps for folding an instrument tray (20) into a packaging material (19) by means of a device (21) according to the invention. FIGS. 2a-d here show a side view of the steps which are performed in a first horizontal folding direction, and FIGS. 2e-2i show a top view of the steps which are performed in a second horizontal folding direction which stands substantially perpendicularly to the first horizontal folding direction. The corresponding reference numerals in FIGS. 2a-2i are assigned to the corresponding parts.

Figure 2A:
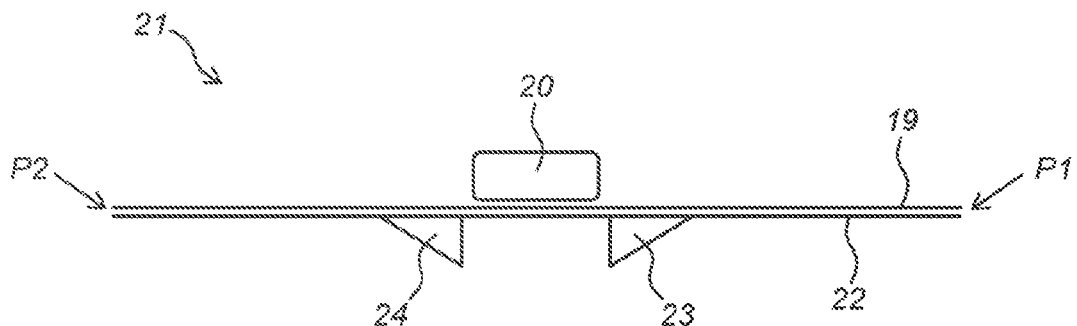

FIG. 2a shows an instrument tray (20) which is positioned on a packaging material (19) on a supporting surface (22). The device (21) shows a first folding plate (23) and a second folding plate (24) which are each located in a first position, wherein the folding plates (23, 24) are positioned substantially below the supporting surface (22). FIG. 2a shows a side view of the device (21), wherein a first primary side (P1) and a second primary side (P2) of the packaging material (19) are shown.

Figure 2B:
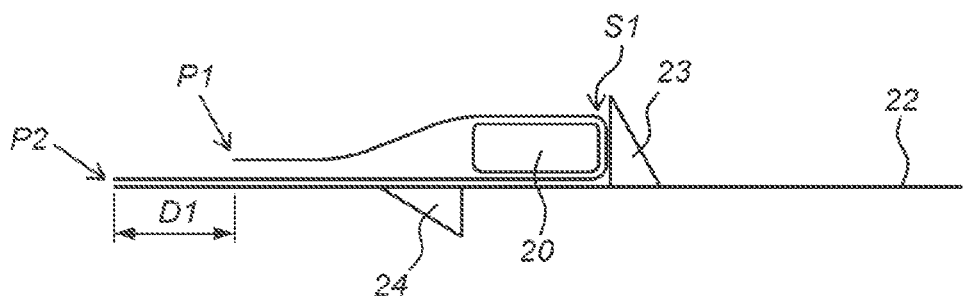

In FIG. 2b, the first primary side (P1) has already been gripped and folded over the instrument tray (20) to a predefined distance (D1) from the second primary side (P2). In this movement of the first primary side (P1) over the instrument tray (20), a first secondary side (S1) is thus formed. The first secondary side (S1) here encloses a side wall of the instrument tray (20). Also, the first limit stop (23) in the form of the first folding plate (23) is positioned, which extends from the supporting surface (22) at the level of the first secondary side (S1). The first limit stop (23) prevents movement of the packaging material (19) and the instrument tray (20) in a first direction of the first horizontal folding direction.

Figure 2C:
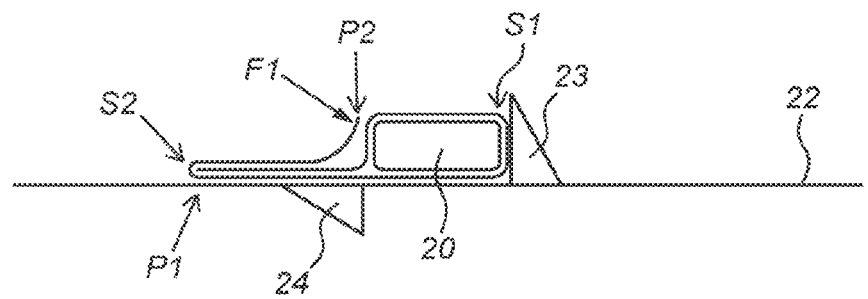

In FIG. 2c, the second primary side (P2) has already been gripped and folded over the first primary side (P1), whereby a second secondary side (S2) is thus formed. The packaging material (19) will then be fixed in the vicinity of a side of the instrument tray (20) facing away from the first limit stop (23); the figure shows a possible preferred position for fixing the packaging material (19), referenced F1. If fixing takes place at the indicated fixing position (F1), an additional turn of the packaging material (19) is created.

Figure 2D:
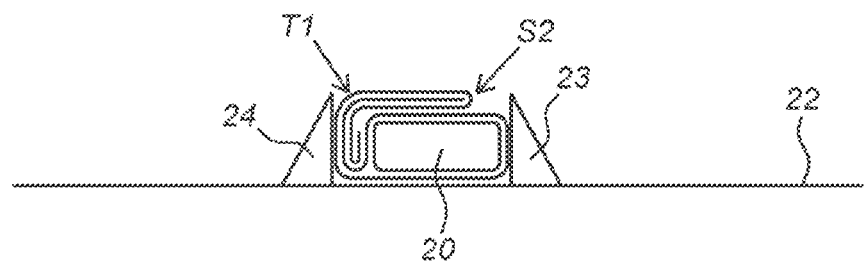

FIG. 2d shows the last step of the folding process of the packaging material (19) in the folding direction shown in FIGS. 2a-2d. Here, the second secondary side (S2) has already been gripped and folded at fixing position F1, so that the second secondary side (S2) is positioned on a top side of the instrument tray (20), whereby a tertiary side (TI) is formed. The second limit stop (24) or the second folding plate (24) has been positioned, wherein the limit stop (24) extends from the supporting surface (22) at the level of the tertiary side (TI). The second limit stop (24) prevents movement of the packaging material (19) and the instrument tray (20) in the second direction of the first horizontal folding direction. FIG. 2d shows the labyrinth structure of the folding packaging material (19). The figure shows however only a diagrammatic depiction, although in practice the packaging material (19) may also not be folded completely tightly because this counters the sterilisation process to be performed later. Pulling the packaging material (19) tight and/or packing the instrument tray (20) too tightly in the packaging material (19) results in undesirable risks of damage to the packaging material.

Figure 2E:
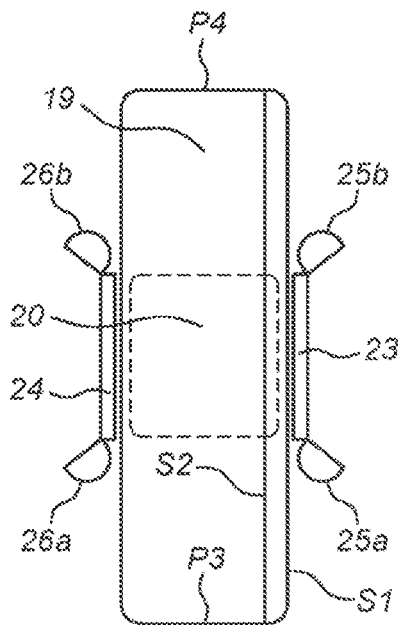

FIG. 2e shows a top view of the situation as obtained by performing method steps 2a-2d. The instrument tray (20) is now enclosed in the packaging material (19) on two sides. The third primary side (P3) and the fourth primary side (P4) are yet to be folded. The first holding plate (23) and the second folding plate (24) are provided with folding parts (25a, 25b, 26a, 26b) fitted with pusher elements (25a, 25b, 26a. 26b). In the embodiment shown, the pusher elements (25a, 25b, 26a, 26b) form an integral part of the folding parts (25a, 25b, 26a, 26b).

Figure 2F:
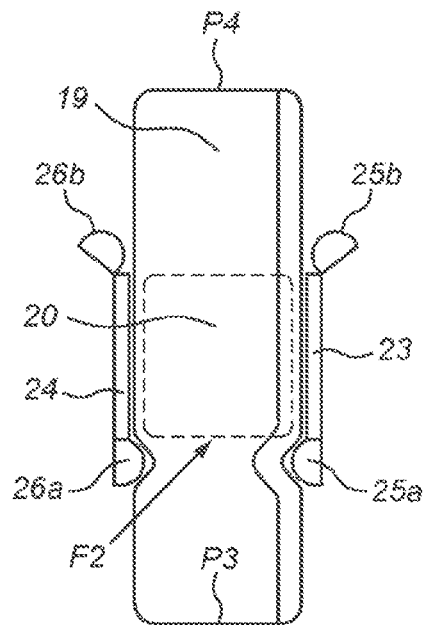

In FIG. 2f, two pusher elements (25a. 26a) are moved about a pivot axis such that the pusher elements (25a, 26a) push the packaging material (19) located outside an area limited by the folding plates (23, 24) at least partially towards an area located between the intersection lines (not shown). In this way, an inward bend in the packaging material (19) is obtained. The figure also shows a preferred position of a later fixing position (F2). The packaging material (19) will be fixed near the instrument tray (20) over a line portion in line with the third primary side (P3) at the level of F2. Such a fixing may be performed for example using the folding aid (not shown).

Figure 2G:
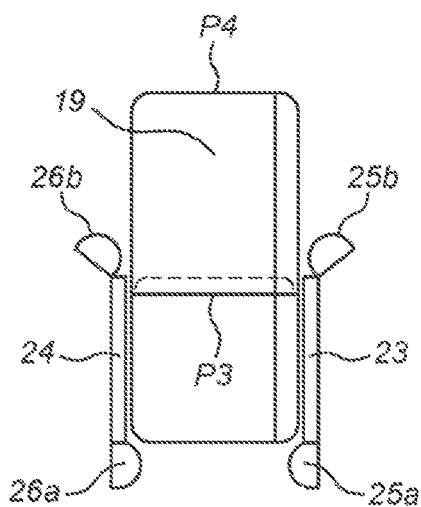

In FIG. 2g, the third primary side (P3) of the packaging material (19) has already been folded up, wherein the third primary side (P3) is positioned on a top side of the instrument tray (20). It is also conceivable that the third primary side (P3) is positioned at a distance above the instrument tray (20) close to the fourth primary side (P4).

Figure 2H:
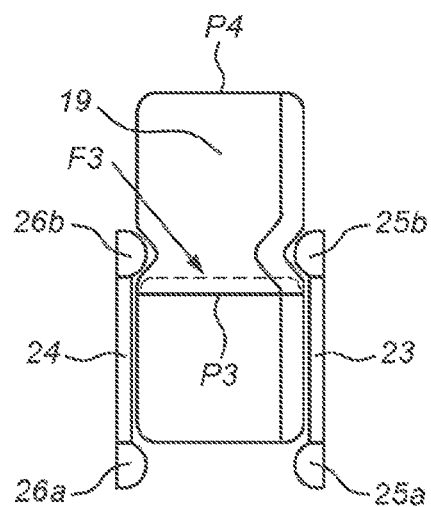

In FIG. 2h, two further pusher elements (25b, 26b) are moved about a pivot axis so that the pusher elements (25b, 26b) push the packaging material (19) located outside an area limited by the folding plates (23, 24) at least partially into an area located between the intersection lines (not shown). The figure also shows a preferred position for a third fixing position (F3) for fixing the packaging material (19) over a line portion in line with the fourth primary side (P4) close to the instrument tray (20).

Figure 2I:
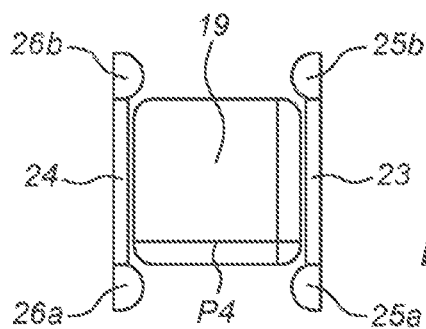

In FIG. 2i, the fourth primary side (P4) of the packaging material (19) has already been folded up, wherein the fourth primary side (P4) is positioned on a top side of the instrument tray (20). In addition, means may then be arranged for fixing the packaging material (19) in the position shown relative to the instrument tray (20).

FIGS. 3a-c show a diagrammatic depiction of possible embodiments of a pusher element (30a, 30b, 30c) for use in a device according to the invention (not shown). The pusher element (30a, 30b, 30c) is configured for pushing a part of the packaging material extending outside an area limited by the folding plates towards an area located between the intersection lines. The figures each show a cross-section, wherein the pusher element (30a. 30b, 30c) is positioned on a supporting surface (31a, 31b, 31c). FIG. 3a shows a first possible embodiment in which the pusher element (30a) with height h1 is shown to be substantially drop-shaped. The pusher element (30a) here comprises a protrusion with an undulating form. The undulating form helps prevent the packaging material from being damaged during folding when it comes into contact with pusher element (30a). The curvature of the drop-shaped pusher element (30a) begins at a predefined distance x1 relative to the supporting surface (31a).

FIG. 3b shows a second embodiment in which the pusher element (30b) with height h2 is provided with a protrusion in the form of a substantially round bulge. The protrusion of the pusher element (30b) is positioned on a top part of the pusher element (30b) viewed relative to the supporting surface (31b). The bottom part of the pusher element (31b) has a substantially flat shape. The protrusion or bulge of the pusher element (30b) is here placed at a predefined distance x2 from the supporting surface (31b).

FIG. 3c shows a third possible embodiment in which the pusher element (30c) with height h3 is provided with a protrusion with an angular form. The angular pusher part is here placed at a predefined distance x3 viewed from the supporting surface (31c) on which the pusher element (30c) is positioned.

FIGS. 4a and 4b show a side view of a second possible embodiment of the folding device (41) according to the invention. The folding device (41) is an alternative to the folding device (21) shown in FIGS. 2a-2i. The steps which are performed in the first horizontal folding direction, as shown completely in FIGS. 2a-d, may also be performed with this.

FIG. 4a shows an instrument tray (40) which is positioned on a packaging material (49) on a supporting surface (42). The device (41) shows a first folding plate (43) and a second folding plate (44) which are each located in a first position, wherein the folding plates (43, 44) leave the supporting surface (42) partially free. The free part is here at least equal to a surface spanned by the packaging material (49). FIG. 4a shows a side view of the device (41), wherein a first primary side (P1) and a second primary side (P2) of the packaging material (49) are shown. Below the respective first folding plate (43) and second folding plate (44), a first magnet (45) and a second magnet (46) are positioned which are responsible for the movement of the first folding plate (43) and the second folding plate (44) between the first and second positions. The first holding plate (43) and the second folding plate (44) are at least partially magnetic. In FIG. 4b, the first primary side (P1) of the packaging material (49) has already been partially moved.

The second primary side (P2) is still in the initial position. The first folding plate (43) moves towards a second position in order to form a first limit stop (43). The movement direction is here indicated with an arrow. The movement takes place under the influence of the first magnet (45).

FIGS. 5a and 5b show a side view of a third possible embodiment of the folding device (41) according to the invention. The folding device (51) is an alternative to the folding devices (21, 41) as shown in FIGS. 2a-2i and 4a-4b. The steps which are performed in a first horizontal folding direction, as shown completely in FIGS. 2a-d, can be performed with this.

FIG. 5a shows an instrument tray (50) which is positioned on a packaging material (59) on a supporting surface (52). The device (51) shows a first folding plate (53) and a second folding plate (54) which are each located in a first position, wherein the folding plates (53, 54) leave the supporting surface (52) partially free. The first (53) and second folding plates (54) are here arranged so as to be translatable relative to the supporting surface (52). The free part is here at least equal to a surface spanned by the packaging material (59). FIG. 5a shows a side view of the device (51), wherein a first primary side (P1) and a second primary side (P2) of the packaging material (59) are shown in an initial state. In FIG. 5b, the first primary side (P1) of the packaging material (59) has already been partially moved. The second primary side (P2) is still in the initial position. The first folding plate (53) moves in the direction of the second position in order to form a first limit stop (53). The movement direction is here indicated with an arrow. The movement takes place under the influence of a mechanical arm (55). The movement of the second folding plate (54) may also take place under the influence of a mechanical arm (56).

FIGS. 6a and 6b show a side view of a fourth possible embodiment of the folding device (61) according to the invention. The folding device (61) is an alternative to the folding devices (21, 41, 51) shown in FIGS. 2a-2i, 4a-4b and 5a-5b. The steps which are performed in a first horizontal folding direction, as shown completely in FIGS. 2a-d, can be performed with this.

FIG. 6a shows an instrument tray (60) which is positioned on the packaging material (69) on a supporting surface (62). The device (61) shows a first folding plate (63) and a second folding plate (64) which are each located in a first position, wherein the folding plates (63, 64) leave the supporting surface (62) partially free. The free part is here at least equal to a surface spanned by the packaging material (69). FIG. 6a shows a side view of the device (61), wherein a first primary side (P1) and a second primary side (P2) of the packaging material (69) are shown in an initial state. In FIG. 6b, the first primary side (P1) of the packaging material (69) has already been partially moved. The second primary side (P2) is still in the initial position. The first folding plate (63) moves in the direction of the second position in order to form a first limit stop (63). The movement direction is here indicated with an arrow. The movement takes place under the influence of an upward force, for example using air pressure.

The present invention is not limited to the exemplary embodiments shown and described here, but within the context of the attached claims, many variants are possible which will be evident to the person skilled in the art.

What is claimed:

1. A device for folding an instrument tray into a packaging material, comprising:
    a supporting surface for supporting the instrument tray during folding of the instrument tray into the packaging material;
    at least one first folding element which is movable between:
        a second position in which the first folding element extends substantially perpendicularly to the supporting surface for forming a limit stop against the movement of the instrument tray and defines a first intersection line with the supporting surface; and
        a first position in which the supporting surface is free and flat at the level of the first intersection line;
    at least one second folding element which is movable between:
        a second position in which the second folding element extends substantially perpendicularly to the supporting surface for forming a limit stop against the movement of the instrument tray and defines a second intersection line with the supporting surface; and
        a first position in which the supporting surface is free and flat at the level of the second intersection line,
    wherein the first intersection line and the second intersection line are substantially parallel to each other;
    a control unit for controlling the movement of the first folding element between its respective first and second positions and the movement of the second folding element between its respective first and second positions,
    wherein a pusher element is provided close to at least one end of a folding element for pushing a part of the packaging material towards an area located between the intersection lines.

2. The device according to claim 1, wherein the control unit is configured for controlling the movement of the pusher element.

3. The device according to claim 1, wherein part of the pusher is formed by protrusion situated at distance from the support surface.

4. The device according to claim 1, wherein at least part of the pusher element has an angular form.

5. The device according to claim 1, wherein at least part of the at least one first folding element and/or the at least one second folding element is formed by a plate, an L-shape, a triangle shape and/or a block.

6. The device according to claim 1, wherein a first pusher element is provided close to at least one end of the at least one first folding element and/or wherein a second pusher element is provided close to at least one end of the at least one second folding element.

7. The device according to claim 1, wherein the at least one first folding element in the first position is positioned at a distance from the first intersection line and/or wherein the at least one second folding element in the first position is positioned at a distance from the second intersection line.

8. The device according to claim 1, comprising a movable folding aid for fixing the packaging material over a predefined line portion before and/or during the making of a fold.

9. The device according to claim 8, wherein the control unit is configured for controlling the movement of the folding aid.

10. The device according to claim 8, wherein the folding aid has an at least partially flat shape.

11. The device according to claim 1, comprising at least one movable clamp for gripping and moving the packaging material.

12. The device according to claim 11, wherein the control unit is configured for controlling the movement and clamping and release of the at least one clamp.

13. The device according to claim 1, wherein the first and/or second folding element is arranged so as to be translatable relative to the supporting surface.

14. The device according to claim 1, comprising at least one movable magnet provided below the supporting surface for moving the first folding element, the second folding element and/or the pusher element.

15. The device according to claim 1, wherein the first and the second intersection lines are positioned at a mutual distance which substantially corresponds to a length or width of an instrument tray to be packed.

16. The device according to claim 1, wherein the distance between the first intersection line and the second intersection line is adjustable.

17. The device according to claim 1, comprising:
a supply means for supplying packaging material; and/or
a supply means for supplying an instrument tray.

18. The device according to claim 17, wherein the supply means for supplying the instrument tray is formed by the at least one clamp.

19. The device according to claim 17, wherein the supply means for supplying packaging material is formed by the at least one clamp.

20. The device according to claim 1, comprising means for establishing a fixing of the packaging material in a predefined position.

* * * * *